US012747274B2

(12) United States Patent
Kim et al.

(10) Patent No.: US 12,747,274 B2
(45) Date of Patent: Sep. 29, 2026

(54) RECOMBINANT VECTOR COMPRISING CODON-OPTIMIZED TIF1γ POLYNUCLEOTIDE, AND USE THEREOF

(71) Applicant: KIM, CELL & GENE CO., LTD., Seoul (KR)

(72) Inventors: Hyo-Soo Kim, Seoul (KR); Eun Ju Lee, Seoul (KR)

(73) Assignee: KIM, CELL & GENE CO., LTD., Seoul (KR)

( * ) Notice: Subject to any disclaimer, the term of this patent is extended or adjusted under 35 U.S.C. 154(b) by 927 days.

(21) Appl. No.: 17/758,853

(22) PCT Filed: Jan. 14, 2021

(86) PCT No.: PCT/KR2021/000554
§ 371 (c)(1),
(2) Date: Jul. 14, 2022

(87) PCT Pub. No.: WO2021/145704
PCT Pub. Date: Jul. 22, 2021

(65) Prior Publication Data

US 2023/0203112 A1 Jun. 29, 2023

(30) Foreign Application Priority Data

Jan. 15, 2020 (KR) ........................ 10-2020-0005239

(51) Int. Cl.

| | |
|---|---|
| ***C07H 21/02*** | (2006.01) |
| ***A61P 1/16*** | (2006.01) |
| ***A61P 11/00*** | (2006.01) |
| ***C07H 21/04*** | (2006.01) |
| ***C07K 14/47*** | (2006.01) |
| ***C12N 15/85*** | (2006.01) |
| *A61K 48/00* | (2006.01) |

(52) U.S. Cl.
CPC ............ *C07K 14/4703* (2013.01); *A61P 1/16* (2018.01); *A61P 11/00* (2018.01); *C12N 15/85* (2013.01); *A61K 48/00* (2013.01); *C12N 2800/22* (2013.01)

(58) Field of Classification Search
CPC .................................................. C07K 14/4703
See application file for complete search history.

(56) References Cited

U.S. PATENT DOCUMENTS

2015/0218242 A1 8/2015 Romeo et al.

FOREIGN PATENT DOCUMENTS

| | | | |
|---|---|---|---|
| KR | 10-1780597 | B1 | 9/2017 |
| KR | 10-2018-0011276 | A | 1/2018 |
| KR | 10-2114880 | B1 | 5/2020 |

OTHER PUBLICATIONS

Wang et al. (Technology in Cancer Research & Treatment, 21, 2022, 1-13).*
Parks et al. (Scientific Reports, 2019, 9:18507, 1-6).*
Zeng et al. (Frontiers in Pharmacology, 2022, 13:1069204, 1-22).*
Chen et al., "TRIM66 reads unmodified H3R2K4 and H3K56ac to respond to DNA damage in embryonic stem cells", Nature communications (2019) 10, 4273, p. 1-17.
Kulkarni et al., "Tripartite Motif-containing 33 (TRIM33) Protein Functions in the Poly(ADP-ribose) Polymerase (PARP)-dependent DNA Damage Response through Interaction with Amplified in Liver Cancer 1 (ALC1) Protein", The Journal of Biological Chemistry, 2013, vol. 288, No. 45, p. 32357-32369.
Ayers et al., "Transforming growth factor-beta signaling in systemic sclerosis", The Journal of Biomedical Research, 2018, vol. 32, No. 1, pp. 3-12.
Ceglia et al., "Preclinical rationale for TGF-beta inhibition as a therapeutic target for the treatment of myelofibrosis", Experimental Hematology, 2016, vol. 44, pp. 1138-1155.
Dewidar et al., "TGF-beta in Hepatic Stellate Cell Activation and Liver Fibrogenesis—Updated 2019", Cells, 2019, vol. 8, Issue 1419, 35 pages.
Huang et al., "CD8+ T cells with high TGF-beta1 expression cause lymph node fibrosis following HIV infection", Molecular Medicine Reports, 2018, vol. 18, pp. 77-86.
Isaka et al., "Targeting TGF-beta Signaling in Kidney Fibrosis", Int. J. Mol. Sci., 2018, vol. 19, Issue 2532, 13 pages.
Ismaeel et al., "Role of Transforming Growth Factor-beta in Skeletal Muscle Fibrosis: A Review", Int. J. Mol. Sci., 2019, vol. 20, Issue 2446, 15 pages.
Jagadeesan et al., "Transforming growth factor beta (TGFbeta) and keloid disease", International Journal of Surgery, 2007, vol. 5, pp. 278-285.
Jagirdar et al., "Transforming Growth Factor-beta (TGF-beta) in Silicosis", Am J Respir Crit Care Med, 1996, vol. 154, pp. 1076-1081.
Kelly et al., "Nephrogenic systemic fibrosis is associated with transforming growth factor beta and Smad without evidence of renin-angiotensin system involvement", J Am Acad Dermatol, 2008, vol. 58, pp. 1025-1030.
Ma et al., "Cardiac fibrosis: new insights into the pathogenesis", Int. J. Biol. Sci., 2018, vol. 14, No. 12, pp. 1645-1657.
Pedroza et al., "Role of STAT3 in skin fibrosis and transforming growth factor beta signalling", Rheumatology, 2018, vol. 57, pp. 1838-1850.

(Continued)

*Primary Examiner* — Amy Rose Hudson
(74) *Attorney, Agent, or Firm* — Vorys, Sater, Seymour and Pease LLP; Mih Suhn Koh

(57) ABSTRACT

Provided is a polynucleotide in which an N-terminal region of TIF1γ gene is codon-optimized, a recombinant vector including the polynucleotide, and a use thereof.

4 Claims, 5 Drawing Sheets

Specification includes a Sequence Listing.

(56) References Cited

OTHER PUBLICATIONS

Ruiz-Ortega et al., "TGF-beta signaling in vascular fibrosis", Cardiovascular Research, 2007, vol. 74, pp. 196-206.
Sielicka et al., "Inhibition of Post-Surgical Repair Mitral Valve Fibrosis Using Transforming Growth Factor-beta Inhibitors", Structural Heart, 2020, vol. 4, No. 51, pp. 190-193.
Van Laethem et al., "Transforming Growth Factor beta Promotes Development of Fibrosis After Repeated Courses of Acute Pancreatitis in Mice", Gastroenterology, 1996, vol. 110, pp. 576-582.
Wang et al., "Emerging roles of transforming growth factor beta signaling in wet age-related macular degeneration", Acta Biochim Biophys Sin, 2018, pp. 1-8.
Watson et al., "Gene delivery of TGF-beta1 induces arthrofibrosis and chondrometaplasia of synovium in vivo", Lab Invest., 2010, vol. 90, No. 11, pp. 1615-1627.
Yue et al., "TGF-beta: Titan of Lung Fibrogenesis", Curr Enzym Inhib., 2010, vol. 6, No. 2, pp. 1-20.

* cited by examiner

RECOMBINANT VECTOR COMPRISING CODON-OPTIMIZED TIF1γ POLYNUCLEOTIDE, AND USE THEREOF

CROSS-REFERENCE TO RELATED APPLICATIONS

This application is a 371 of PCT/KR2021/000554 filed on Jan. 14, 2021, which claims the benefit of priority from Korean Patent Application No. 10-2020-0005239 filed on Jan. 15, 2020, the contents of each of which are incorporated herein by reference in its entirety.

SEQUENCE LISTING

The Sequence Listing submitted in text format (.txt) filed on Jul. 14, 2022, named "SequenceListing.txt", created on Jul. 14, 2022 (10.7 KB), is incorporated herein by reference.

TECHNICAL FIELD

The present invention relates to a recombinant vector including a codon-optimized TIF1γ polynucleotide, and a use thereof.

BACKGROUND ART

A fibrotic disease, that is, fibrosis, collectively refers to a disease in which excessive fibrous connective tissue is formed by the abnormal accumulation of collagen matrix in a regeneration or reaction process, and the form thereof is very different from the formation of normal fibrous tissue. Examples of a representative tissue in which fibrosis occurs include the heart, the kidneys, the liver, fat, the lungs, the heart, bones, bone marrow, and the skin. Cardiac fibrosis is a phenomenon commonly occurring in many heart diseases, includes replacement (scarring) fibrosis, interstitial (reactive) fibrosis, and the like, and includes renal fibrosis, hepatic fibrosis, scleroderma, and the like depending on the location of fibrosis, in addition to the fibrosis described above. Scleroderma is a chronic disease characterized by excessive collagen deposition in the skin or other organs and is known to affect blood vessels and internal organs in severe cases. Skeletal muscle fibrosis is a phenomenon that is primarily induced in injured muscles and is characterized by overgrowth of fibrous tissue, primarily caused by the body's attempts to recover from the injury. In particular, recently, pulmonary fibrosis caused by polyhexamethylene guanidine (PHMG) and oligo(2-)ethoxy ethoxyethyl guanidine chloride (PGH) contained in humidifier disinfectants occurred, consequently, causing deaths and becoming a social issue.

Most fibrosis is a disease that is not only highly diverse in pathogenic factors and pathways, but also manifested by repetitive actions, and the mechanism itself has not been clearly identified, so the development of effective drugs for treatment is insufficient (Korean Patent Application Laid-Open No. 10-2019-0003422).

Although examples of an anti-inflammatory agent known to be partially helpful for the treatment of fibrosis include prednisone, glucocorticoids, and the like, the therapeutic effect or stability thereof has not been verified, and there are attempts to use cells differentiated from stem cells with high proliferative capacity instead of tissue transplantation, but it is still difficult to apply this to direct treatment because, in vivo, the cell survival rate is low or there is a risk of causing immune rejection. In addition, although methods such as suppression of fibrosis factor activity and extracellular matrix degradation are known for the treatment of fibrosis, not only are the methods still used for direct treatment rare, but also is it difficult to completely treat fibrosis due to the chronic progression of the fibrosis process.

Therefore, there is an urgent need for the development of a substantially commercially viable therapeutic agent that exhibits a remarkable therapeutic effect on various fibrotic diseases.

DISCLOSURE

Technical Problem

The present invention has been made in an effort to solve the problems in the related art as described above, and an object thereof is to provide a polynucleotide encoding a codon-optimized TIF1γ, a recombinant vector including the same, a use of the recombinant vector, and the like.

However, the technical problems which the present invention intends to solve are not limited to the technical problems which have been mentioned above, and other technical problems which have not been mentioned will be apparently understood by a person with ordinary skill in the art to which the present invention pertains from the following description.

Technical Solution

The present invention provides a polynucleotide in which the N-terminal region of a transcriptional intermediary factor 1 gamma (TIF1γ) gene is codon-optimized. The N-terminus may refer to a gene region corresponding to 359 bp to 1670 bp of the TIF1γ gene, and the codon optimization refers to an optimized sequence in human cells. Preferably, the polynucleotide may include a nucleic acid sequence of SEQ ID NO: 2, may include more preferably base sequences of SEQ ID NOS: 2 and 3, and may include even more preferably a nucleic acid sequence of SEQ ID NO: 1. Further, the polynucleotide of the present invention includes a variant of SEQ ID NO: 1, 2, 3 or 4 within the scope of the present invention. Specifically, the polynucleotide may include a nucleic acid sequence having a sequence homology of 90% or more, more preferably 95% or more, and most preferably 98% or more to a nucleic acid sequence of SEQ ID NO: 1, 2, 3 or 4. The "% sequence homology" to a polynucleotide is confirmed by comparing a comparison region with an optimally aligned sequence, and a portion of the polynucleotide sequence in the comparison region may further include an addition or deletion (that is, a gap) compared to the reference sequence (without an addition or deletion) for the optimal alignment of the sequence.

In addition, the present invention provides a recombinant vector including the polynucleotide. The recombinant vector may also be used for producing a TIF1γ recombinant protein.

Furthermore, the present invention provides a pharmaceutical composition for preventing or treating a fibrotic disease, including the polynucleotide or recombinant vector.

Further, the present invention provides a method for preventing or treating a fibrotic disease, the method including administering a composition including the polynucleotide or recombinant vector as an active ingredient to a subject in need.

In addition, the present invention provides a use of a composition including the polynucleotide or recombinant vector as an active ingredient for preventing or treating a fibrotic disease.

Furthermore, the present invention provides a use of the polynucleotide or recombinant vector for producing a drug used for preventing or treating a fibrotic disease.

In an exemplary embodiment of the present invention, the fibrotic disease is preferably hepatic fibrosis, renal fibrosis, pulmonary fibrosis, pancreatic fibrosis, systemic scleroderma, macular degeneration, cardiac fibrosis, pancreatic and pulmonary cystic fibrosis, injection fibrosis, endomyocardial fibrosis, idiopathic systemic fibrosis, idiopathic pulmonary fibrosis, mediastinal fibrosis, myelofibrosis, retroperitoneal fibrosis, progressive massive fibrosis, nephrogenic systemic fibrosis, nodular subepithelial fibrosis, breast fibrosis, lymph nodal fibrosis, scarring, scleroderma, skin fibrosis, bladder fibrosis, muscle fibrosis, arterial fibrosis, chronic obstructive pulmonary disease, thyroid gland fibrosis, arthrofibrosis, pleural fibrosis, fibrosis as a result of surgery, proliferative fibrosis, pipe-stem fibrosis, postfibrinous fibrosis, and the like, and is more preferably hepatic fibrosis, but is not limited thereto as long as it is a fibrotic disease that can be treated by the expression of the TIF1γ protein.

Advantageous Effects

Since a polynucleotide in which the N-terminal region of the TIF1γ gene according to the present invention is codon-optimized can remarkably increase the production amount of a TIF1γ recombinant protein by suitably modifying the N-terminal region for human cells, it was confirmed that not only the polynucleotide can be used for producing the TIF1γ recombinant protein, but also the therapeutic effect on a fibrotic disease using a recombinant vector into which the polynucleotide is inserted is increased, so the polynucleotide of the present invention is expected to be used as a stable and effective therapeutic agent for the treatment of various fibrotic diseases because the polynucleotide of the present invention can be widely used in various fields where the TIF1γ recombinant protein can be used and can prevent and treat fibrotic diseases by increasing the expression level of the TIF1γ protein.

MODES OF THE INVENTION

Figure 1:
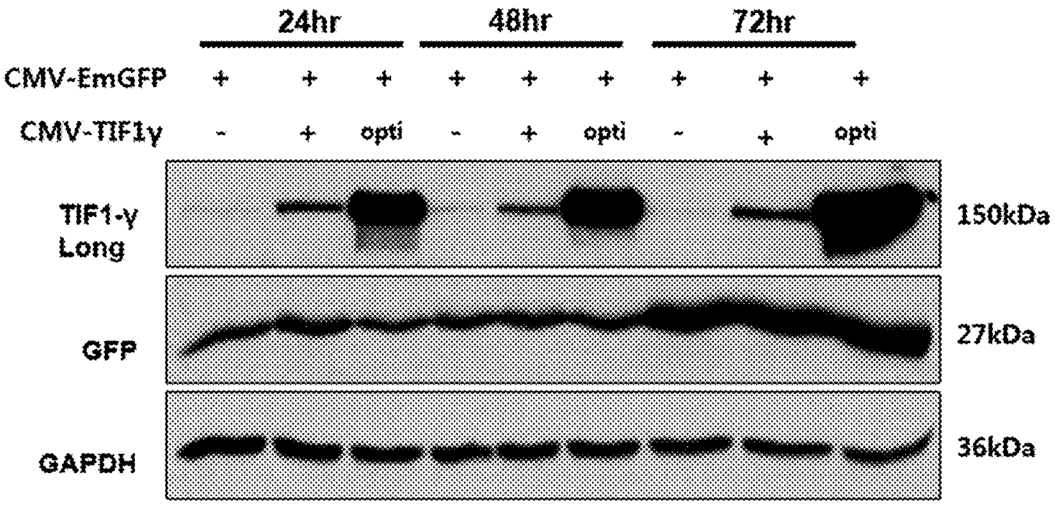
FIG. 1 is a view illustrating the results of comparing the protein expression levels of the TIF1γ gene by codon optimization according to an exemplary embodiment of the present invention.

Since it was confirmed that when a TIF1γ recombinant protein is produced using a polynucleotide in which the N-terminal region of the TIF1γ gene of the present invention is codon-optimized, the production amount of the recombinant protein can be increased using the same amount of gene and this also increases the therapeutic effect on fibrotic diseases, it is expected that the optimized TIF1γ polynucleotide of the present invention can be used and applied to various fields such as the treatment of fibrosis.

As used herein, fibrosis collectively refers to all symptoms in which abnormal accumulation of collagen matrix or formation of excessive fibrous connective tissue occurs in a tissue, and a fibrotic disease (fibrosis) may occur due to such fibrosis, and the location of occurrence is not limited. In general, fibrosis is induced when TGF-β1 binds to receptors on the cell wall surface to activate the Smad signaling mechanism, and as a result, the expression levels of α-smooth muscle actin (α-SMA) and a tissue inhibitor of matrix metalloproteinases (TIMP) are increased to activate myofibroblasts and accumulate the matrix, as described in Nature Reviews Nephrology (2016) 12: 325-338.

In the present specification, transcriptional intermediary factor 1 gamma (TIF1γ) is a gene that is known as a transcriptional factor involved in the cell differentiation and development. The TIF1γ of the present invention can treat fibrosis by suppressing Smad4 or forming a complex with Smad2/3 to suppress the expression of genes that induce fibrosis, such as α-SMA. Therefore, the codon-optimized TIF1γ polynucleotide of the present invention can also effectively suppress the expression of genes that induce fibrosis, such as α-SMA, and thus may be applied to various fibrotic diseases such as pulmonary fibrosis, hepatic fibrosis and renal fibrosis.

As used herein, the "vector" refers to a DNA fragment, nucleic acid molecule, and the like, which are delivered into a cell, and the vector may replicate DNA and be independently re-manufactured in a host cell. The vector may be used interchangeably with the term "carrier". "Expression vector" refers to a recombinant DNA molecule that includes a target coding sequence and an appropriate nucleic acid sequence that is essential for expressing an operably linked coding sequence in a specific host organism. The recombinant vector of the present invention includes a plasmid vector, a cosmid vector, a bacteriophage vector, a viral vector, and the like, but is not limited thereto. A suitable expression vector may include an expression regulatory element such as a promoter, an operator, an initiation codon, a termination codon, a polyadenylation signal, and an enhancer, and may be variously manufactured depending on the purpose. The promoter may preferably be a promoter used to express a protein in human cells, and more preferably, a specific promoter inducing expression in a region where fibrosis is induced, such as the TGF-beta promoter, and the like, but is not limited thereto. As used herein, the "operably linked" refers to a state in which a nucleic acid expression control sequence and a nucleic acid sequence encoding a target protein or RNA are functionally linked so as to carry out a general function. For example, a promoter and a nucleic acid sequence encoding a protein or RNA may be operably linked to affect the expression of the coding sequence. An operable linkage with an expression vector may be prepared using a gene recombination technique well-known in the art, and site-specific DNA cleavage and ligation may use enzymes generally known in the art, or the like.

As used herein, prevention refers to a broad concept of blocking the occurrence of fibrosis, preferably includes both primary prevention to prevent the occurrence of fibrosis in advance, and secondary prevention to early detect and timely treat the occurrence, but is not limited thereto as long as it is a process and/or activity which addresses fibrosis before it occurs.

As used herein, treating refers to a broad concept that deals with the occurrence of fibrosis, and is not limited as long as it is a process and/or activity for treating, healing, alleviating, reducing, and the like fibrosis.

As used herein, a subject in need refers to a subject to which the composition of the present invention may be administered, and the subject is not limited.

As used herein, a pharmaceutical composition may be in the form of a capsule, a tablet, a granule, an injection, an ointment, a powder, or a beverage, and the pharmaceutical composition may be characterized in that it targets humans. However, the pharmaceutical composition is not limited thereto and may be formulated into the form of an oral dosage form such as powder, granules, a capsule, a tablet, and an aqueous suspension, an external preparation, a suppository, and a sterile injectable solution. The pharmaceutical composition of the present invention may include a pharmaceutically acceptable carrier. As the pharmaceutically acceptable carrier, a binder, a lubricant, a disintegrant, an excipient, a solubilizing agent, a dispersing agent, a stabilizer, a suspending agent, a colorant, a flavoring agent, and the like may be used when orally administered, in the case of injection, a buffering agent, a preservative, an analgesic, a solubilizer, an isotonic agent, a stabilizer, and the like may be mixed and used, and in the case of topical administration, a base, an excipient, lubricant, a preservative, and the like may be used. The formulation of the pharmaceutical composition of the present invention may be variously prepared by mixing the pharmaceutical composition of the present invention with the pharmaceutically acceptable carrier as described above. For example, the formulation may be prepared in the form of a tablet, a troche, a capsule, an elixir, a suspension, a syrup, a wafer, and the like when orally administered, and in the case of injection, the injection may be formulated into unit dosage ampoules or in multiple dosage forms. The pharmaceutical composition of the present invention may be formulated into other solutions, suspensions, tablets, capsules, sustained-release preparations, and the like.

Meanwhile, as an example of suitable carriers, excipients and diluents for formulation, it is possible to use lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate, mineral oil, or the like. Further, the pharmaceutical composition of the present invention may further include a filler, an anticoagulant, a lubricant, a wetting agent, a flavoring agent, an emulsifying agent, an antiseptic, and the like.

The route of administration of the pharmaceutical composition according to the present invention includes, but is not limited to, oral, intravenous, intramuscular, intraarterial, intramedullary, intrathecal, intracardiac, transdermal, subcutaneous, intraperitoneal, intranasal, enteral, topical, sublingual or rectal administration. Oral or parenteral administration is preferred. As used herein, the term “parenteral” includes subcutaneous, intradermal, intravenous, intramuscular, intraarticular, intrasynovial, intrasternal, intrathecal, intralesional administration and intracranial injection or infusion techniques. The pharmaceutical composition of the present invention may also be administered in the form of a suppository for rectal administration.

The pharmaceutical composition of the present invention varies depending on various factors including the activity of the specific compound used, age, body weight, general health, sex, diet, time of administration, route of administration, rate of excretion, drug combination and the severity of the particular disease to be prevented or treated, and the dosage of the pharmaceutical composition varies depending on the condition of the patient, the body weight, the degree of disease, the form of drug, the route of administration and duration, but may be appropriately selected by a person skilled in the art, and may be 0.0001 to 500 mg/kg or 0.001 to 500 mg/kg daily. The administration may be carried out once daily, and may be divided into several times. The dosage is not intended to limit the scope of the present invention in any way. The pharmaceutical composition according to the present invention may be formulated into pills, dragees, capsules, solutions, gels, syrups, slurries, and suspensions.

Hereinafter, preferred examples for helping the understanding of the present invention will be suggested. However, the following examples are provided only to more easily understand the present invention, and the contents of the present invention are not limited by the following examples.

EXAMPLES

Example 1: TIF1γ Codon Optimization

Codon optimization of TIF1γ was performed to maximize the expression of a TIF1γ recombinant protein. In order to confirm the difference in the production amount of recombinant protein according to codon optimization, three types of sequences, in which the entire nucleotide sequence of TIF1γ (Sequence ID: NM_015906) was specifically optimized as gene codons that are frequently expressed in human cells, were prepared. Then, each TIF1γ gene was inserted into pVAX1 (Thermo Fisher) and expressed in a 293T cell line. The original sequence of TIF1γ was used as a control. Further, the efficiency of transfection was compared by transfection with a CMV-emGFP vector. Then, the expressed TIF1γ recombinant protein was confirmed by western blotting. For the western blotting, collected cells were lysed in 0.10% sodium dodecyl sulfate containing a protein lysis buffer (50 mM Tris-HCl, 150 mM NaCl, 0.5% deoxycholate, 1% NP40 and a protease inhibitor cocktail (Roche)), 25 to 30 μg of a protein extract was heated at 95° C. for 5 minutes, and then SDS-page was performed. Then, after SDS-page was completed, proteins separated by size were transferred to polyvinylidene fluoride membranes (Millipore) using a BioRad transfer unit (BioRad). Then, the membranes were blocked using 5% skim milk and then reacted using a TIF1γ antibody (Thermo Fisher Scientific), and an anti-GAPDH antibody (ABcam) was used as an internal control. The membrane reacted using the antibodies was washed to remove the unbound antibodies, then reacted using horseradish peroxidase-conjugated secondary antibodies, and bands were confirmed using enhanced chemiluminescence (ThermoFisher). The results are illustrated in FIG. 1.

As illustrated in FIG. 1, it was confirmed that in the TIF1γ recombinant protein (opti) of SEQ ID NO: 1 among the three codon-optimized sequences, the protein production amount was increased 10-fold or more when compared to the original sequence (+).

Further, in order to confirm whether the protein expression level varied according to codon optimization of a partial sequence rather than the entire sequence of TIF1γ, based on the codon-optimized sequence of SEQ ID NO: 1, the entire sequence of TIF1γ having a part of the N-terminal portion corresponding to 359 bp to 1670 bp replaced with an optimized sequence (SEQ ID NO: 2), the entire sequence of TIF1γ having a part of the C-terminal portion corresponding to 2560 bp to 3382 bp replaced with an optimized sequence (SEQ ID NO: 3), and the entire sequence of TIF1γ having SEQ ID NOS: 2 and 3 replaced with an optimized sequence (SEQ ID NO: 4) were prepared, inserted into pVAX1, and allowed to be expressed in a 293T cell line for 24 hours. Then, the expressed TIF1γ recombinant protein was confirmed by western blotting, and each band was quantified using ImageJ software. The results are illustrated in FIG. 2.

Figure 2:
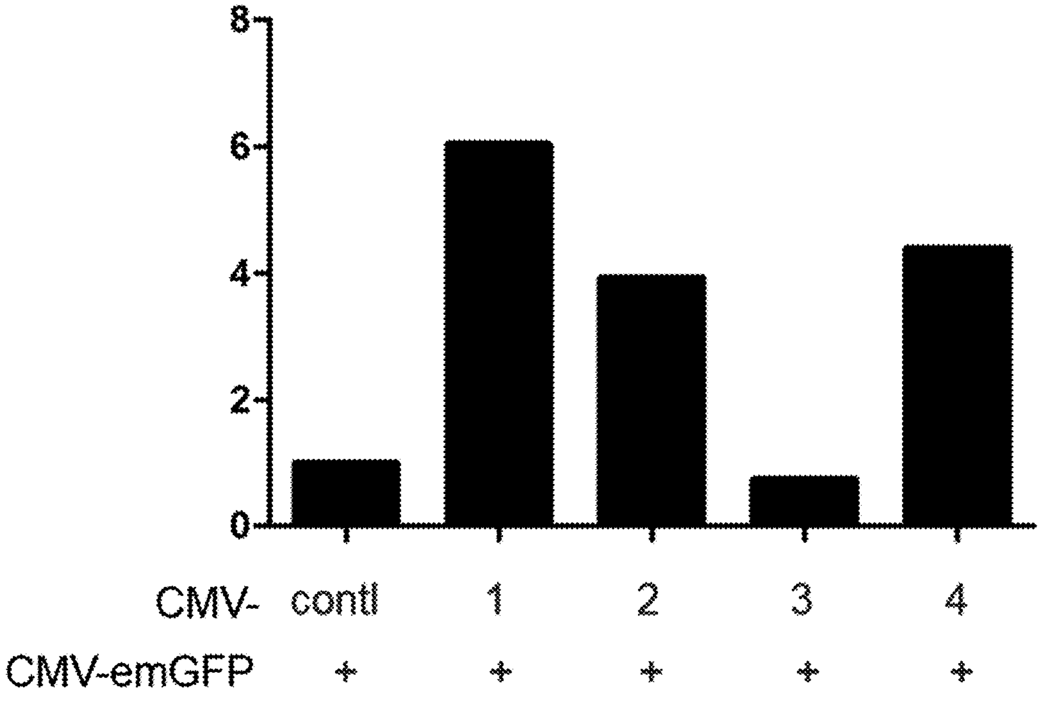
FIG. 2 is a view illustrating the results of comparing the protein expression levels of the TIF1γ gene by codon optimization for each region according to an exemplary embodiment of the present invention.

As illustrated in FIG. 2, it was confirmed that the protein expression level of the polynucleotide (1) in which the entire sequence of TIF1γ was codon-optimized was the highest, and the polynucleotide (2) in which only the N-terminus was codon-optimized and the polynucleotide (4) in which the N-terminus and C-terminus were codon-optimized had a protein expression level increased 4-fold or more compared to a control in which the original sequence of the TIF1γ gene was used. However, it was confirmed that the polynucleotide (3) in which only the C-terminus was codon-optimized showed almost the same expression level as that of the original sequence. Through the above results, it was confirmed that the codon optimization of the N-terminus plays an important role in the expression level of a TIF1γ recombinant protein.

Example 2: Confirmation of Therapeutic Effect of TIF1γ Recombinant Protein on Hepatic Fibrosis Disease In order to confirm the therapeutic effect of the TIF1γ recombinant protein produced by codon optimization on a hepatic fibrosis disease, a human hepatic stellate cell line LX2 was transfected with a vector constructed in the same manner as in Example 1. Then, the transfected cells were treated with TGFβ at a concentration of 5 ng/mL daily for 7 days. Then, the cells were collected and protein expression levels were confirmed by western blotting. Western blotting was performed in the same manner as in Example 1, and an α-SMA (Abcam) or Col1A (Abcam) antibody was used as a primary antibody. The results are illustrated in FIG. 3.

Figure 3:
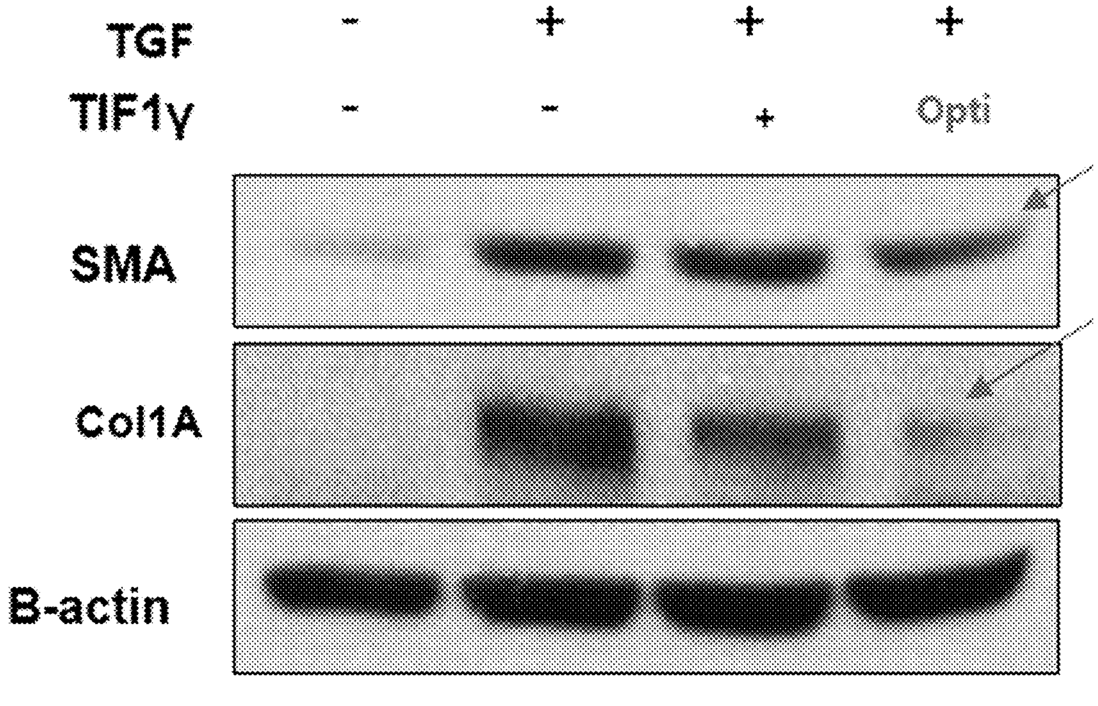
FIG. 3 is a view illustrating the results of confirming the therapeutic effect of the codon-optimized recombinant gene of the TIF1γ gene according to an exemplary embodiment of the present invention on fibrotic diseases.

As illustrated in FIG. 3, it was confirmed that the expression level of SMA and Col1A, known as fibrotic factors, was increased when cells were treated with TGFβ, the expression level of SMA and Col1A was slightly reduced when cells were transfected with a vector (+) using the original sequence of the TIF1γ gene, and the expression level of SMA and Col1A was further effectively reduced when cells were transfected with a vector (Opti) using a polynucleotide in which the entire sequence of TIF1γ was codon-optimized compared to that of a vector using the original sequence. Through the above results, it was confirmed that the TIF1γ recombinant protein produced by codon optimization showed a fibrosis inhibitory effect as in the case of using the original sequence of the TIF1γ gene, and when cells were transfected with the same amount of vector, the protein expression level in the codon-optimized TIF1γ recombinant increased, and thus the fibrosis therapeutic effect also increased.

Figure 4:
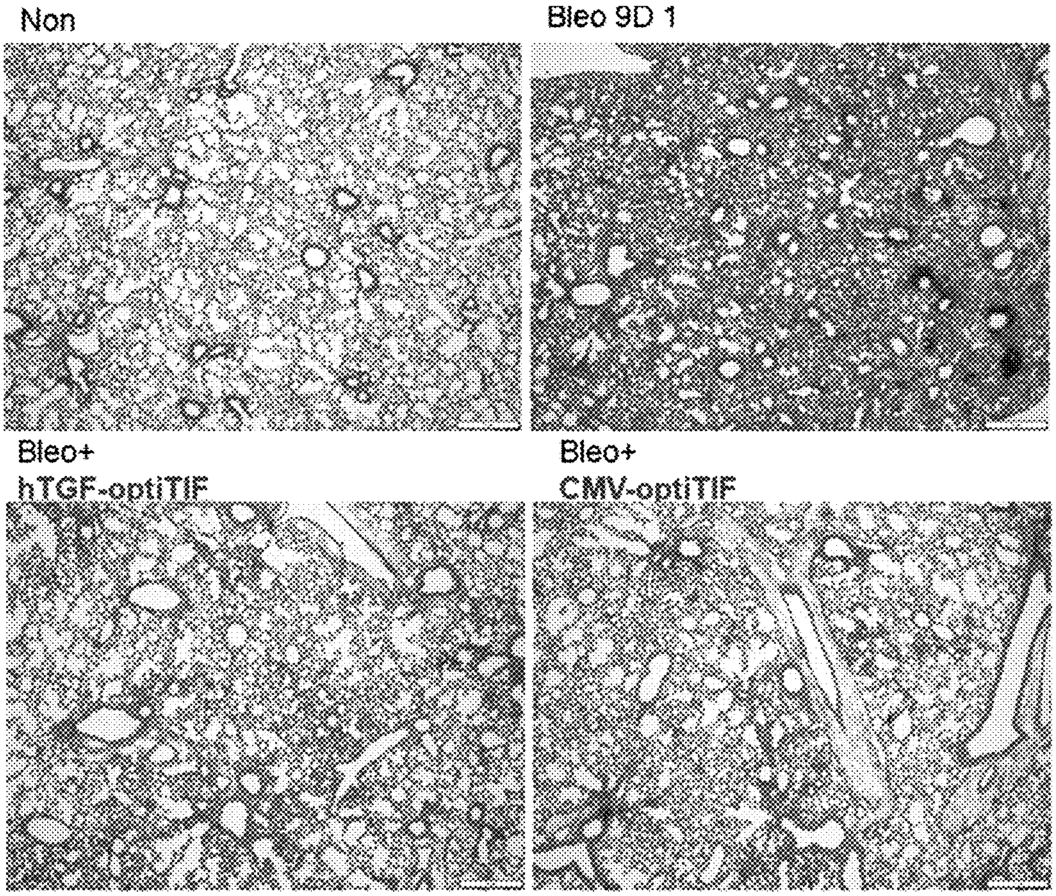
FIG. 4 is a view illustrating the results of confirming the therapeutic effect of the codon-optimized recombinant gene of the TIF1γ gene according to an exemplary embodiment of the present invention on fibrotic diseases by H&E staining.

Example 3: Confirmation of Therapeutic Effect of TIF1γ Recombinant Protein on Pulmonary Fibrosis Disease In order to confirm the therapeutic effect of the TIF1γ recombinant protein produced by codon optimization on a pulmonary fibrosis disease, a pulmonary fibrosis animal model was produced by primary treatment with bleomycin. More specifically, bleomycin was injected into 5- to 8-week-old C57BL/6N mouse at a concentration of 2 mg/kg by endotracheal administration, and 9 days later, 18 g/mouse of a vector constructed in the same manner as in Example 1 was injected via the tail vein. A CMV promoter or a human TGF beta promoter (hTGF) of SEQ ID NO: 5 was used as a promoter sequence of the vector. Then, 21 days later, the mice were euthanized and lung tissue was obtained. The obtained right lung tissue was fixed using a 10% formalin solution, then embedded using paraffin, and cut to a thickness of 4 μm to prepare tissue sections. Then, after the paraffin was removed from the prepared tissue section, immunostaining was performed using hematoxylin and eosin, and then the tissue section was observed using a microscope. The results are illustrated in FIG. 4. Then, the obtained left lung tissue was stained using a Masson's trichrome (MT) stain kit (Abcam). The results are illustrated in FIG. 5.

As illustrated in FIG. 4, it was confirmed that in the lung tissue (Bleo9D1) treated with bleomycin, fibrosis was induced by bleomycin, and when a vector (hTGF-optiTIF or CMV-optiTIF) using a polynucleotide in which the entire sequence of TIF1γ was codon-optimized was injected, fibrosis was reduced.

Figure 5:
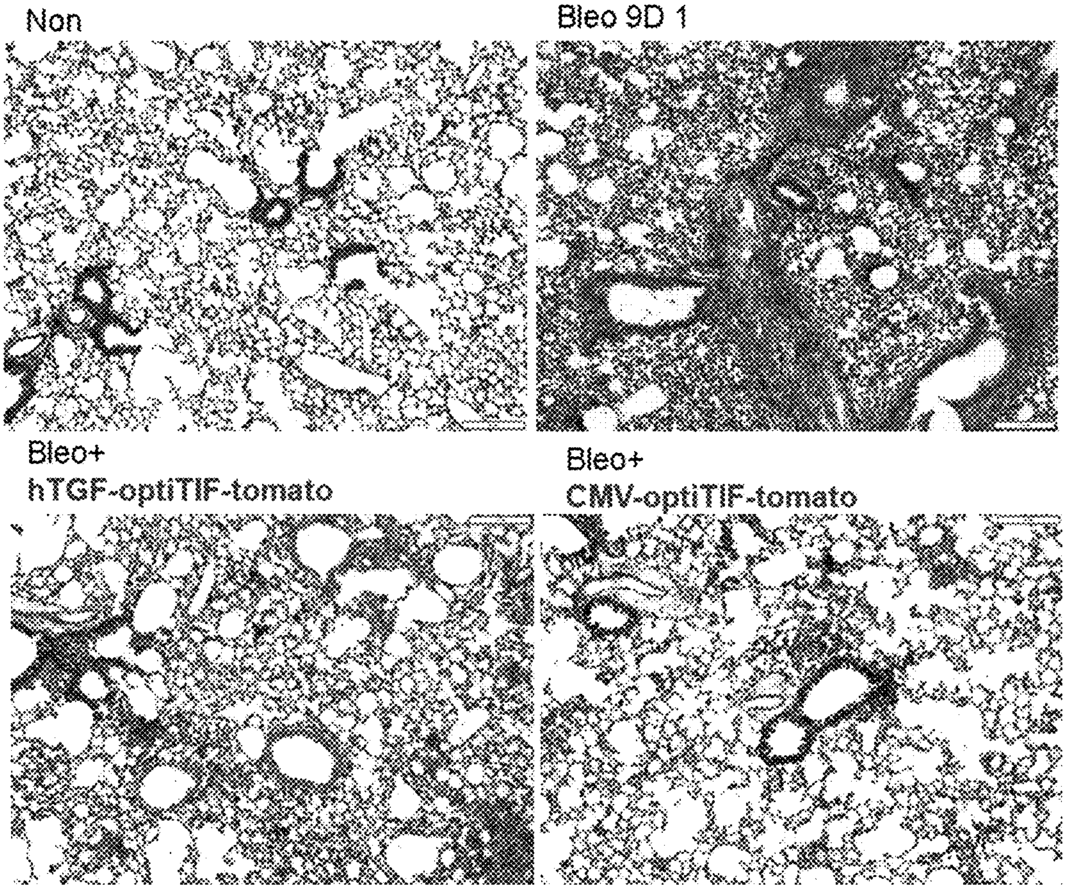
FIG. 5 is a view illustrating the results of confirming the therapeutic effect of the codon-optimized recombinant gene of the TIF1γ gene according to an exemplary embodiment of the present invention on fibrotic diseases by MT staining.

As illustrated in FIG. 5, it was confirmed that in the lung tissue (Bleo9D1) treated with bleomycin, fibrosis was induced by bleomycin, and when a vector (hTGF-optiTIF or CMV-optiTIF) using a polynucleotide in which the entire sequence of TIF1γ was codon-optimized was injected, fibrosis was reduced.

Through the above results, it could be confirmed that fibrosis could be treated using a polynucleotide in which the entire sequence of TIF1γ of the present invention was codon-optimized.

Through the above results, it could be confirmed that when the codon-optimized TIF1γ polynucleotide of the present invention was used, the production amount of the TIF1γ recombinant protein could be increased, and the protein expression level could be increased even though a small amount of vector was injected by using a vector including the codon-optimized TIF1γ polynucleotide, thereby remarkably increasing the therapeutic effect on fibrotic diseases.

The above-described description of the present invention is provided for illustrative purposes, and those skilled in the art to which the present invention pertains will understand that the present invention can be easily modified into other specific forms without changing the technical spirit or essential features of the present invention. Therefore, it should be understood that the above-described embodiments are only exemplary in all aspects and are not restrictive.

INDUSTRIAL APPLICABILITY

Since a polynucleotide in which the N-terminal region, C-terminal region or entire sequence of the TIF1γ gene according to the present invention is codon-optimized can remarkably increase the production amount of TIF1γ recombinant protein, and it is possible to effectively treat fibrotic diseases using the polynucleotide, the polynucleotide is expected to be widely applied to the treatment of various fibrotic diseases and used as a stable and effective therapeutic agent.

The invention claimed is:

1. A polynucleotide consisting of the nucleic acid set forth in SEQ ID NO: 1, wherein the polynucleotide is a codon optimized transcriptional intermediary factor 1 gamma (TIF1γ) gene.

2. A recombinant vector comprising the polynucleotide of claim 1.

3. A method for treating a fibrotic disease, the method comprising administering to a subject in need thereof a composition comprising the polynucleotide of claim 1 as an active ingredient, wherein the fibrotic disease is any one or more selected from the group consisting of a hepatic fibrosis, pulmonary fibrosis, idiopathic pulmonary fibrosis, progressive massive fibrosis, renal fibrosis, and nephrogenic systemic fibrosis.

4. A method for treating a fibrotic disease, the method comprising administering a composition comprising the recombinant vector of claim 2 as an active ingredient to a subject in need, wherein the fibrotic disease is any one or more selected from the group consisting of a hepatic fibrosis, pulmonary fibrosis, idiopathic pulmonary fibrosis, progressive massive fibrosis, renal fibrosis, and nephrogenic systemic fibrosis.

* * * * *

SEQUENCE LISTING

<160> NUMBER OF SEQ ID NOS: 5

<210> SEQ ID NO 1
<211> LENGTH: 3385
<212> TYPE: DNA
<213> ORGANISM: Artificial Sequence
<220> FEATURE:
<223> OTHER INFORMATION: codon optimization of TIF1gamma full sequence

<400> SEQUENCE: 1

```
catggccgag aacaaaggcg gcggagaagc tgaatctggc ggaggcggat ctggatctgc     60

tcctgttaca gctggtgccg ctggacctgc tgctcaagaa gcagaacctc ctctgacagc    120

cgtgctggtg gaagaagaag aggaagaagg cggcagagct ggcgctgaag gcggagctgc    180

tggaccagat gatggcggag ttgccgctgc ctctagtgga tctgcacagg ctgcatctag    240

ccctgccgcc tctgttggaa caggtgttgc tggcggagcc gtgtctacac cagctccagc    300

accagcaagt gctccagctc ctggaccttc tgcaggacct ccacctggac ctccagcttc    360

tctgctggat acctgtgccg tgtgtcagca gagcctgcag agcagaagag aggccgagcc    420

taagctgctg ccttgcctgc acagcttctg cctgagatgt ctgcccgagc ctgagagaca    480

gctgagcgtt ccaattcctg gcggcagcaa cggcgacatt cagcaagtgg gcgtgatcag    540

atgccccgtg tgcagacaag agtgccggca gattgacctg gtggacaact acttcgtgaa    600

ggacaccagc gaggccccta gcagctctga cgagaagtct gagcaagtgt gcacctcctg    660

cgaggacaat gcctctgccg tgggcttctg tgtggaatgt ggcgagtggc tgtgcaagac    720

ctgtatcgag gcccaccaga gagtgaagtt caccaaggac cacctgatcc ggaagaaaga    780

agatgtgtcc gagagcgtgg gcgcctctgg acaaagacct gtgttctgcc ccgtgcacaa    840

gcaagagcag ctgaagctgt tctgcgagac atgcgaccgg ctgacctgca gagattgcca    900

gctgctcgaa cacaaagagc acagatacca gtttctggaa gaggcctttc agaaccagaa    960

gggcgccatc gagaacctgc tggccaaact gctggaaaag aaaaactacg tgcacttcgc   1020

cgccacacag gtgcagaacc ggatcaaaga agtgaacgag acaaacaagc gggtcgagca   1080

agagatcaag gtggccatct tcaccctgat caacgagatc aacaagaagg gcaagagcct   1140

cctgcagcag ctggaaaacg tgaccaaaga acggcagatg aagctgcttc agcagcagaa   1200

cgacatcacc ggcctgagca gacaagtgaa gcacgtgatg aatttcacca actgggccat   1260

tgccagcggc agctctacag ccctgctgta ctccaagcgg ctgatcacct tccagctgag   1320

acacatcctg aaggccagat gcgatcctgt gcctgccgcc aatggcgcta tcagattcca   1380

ctgcgacccc accttttggg ccaagaacgt cgtgaacctg ggcaacctgg tcatcgagag   1440

caagcctgct cctggctaca cccctaatgt ggtcgttgga caggtgccac ctggcaccaa   1500

ccacatctct aagacccctg gccagatcaa cctggctcag ctcagactgc agcacatgca   1560

gcagcaagtg tacgcccaga aacaccagca gctgcagcag atgcggatgc agcaacctcc   1620

tgctccagtg cctaccacca ccacaaccac acagcagcac cctagacagg ccgctcctca   1680

gatgctgcaa cagcagcctc caagactgat cagcgtgcag actatgcagc ggggcaacat   1740

gaactgcgga gcctttcagg cccatcagat gagactggcc cagaacgccg ctagaatccc   1800

tggcatccct agacacagcg gccctcagta cagcatgatg cagccccatc tgcagagaca   1860

gcacagcaat cctggacacg ccggaccttt tccagtggtg tctgtgcaca ataccacgat   1920

caaccctaca agccccacca ccgccacaat ggccaatgcc aatagaggcc caacaagccc   1980

tagcgtgaca gccatcgagc tgatccccag cgtgacaaac cccgagaatc tgcctagcct   2040
```

```
gcctgacatc cctcctatcc agctcgagga tgccggctct agcagcctgg ataatctgct   2100

gagccggtac atcagcggct cccatcttcc acctcagcct accagcacaa tgaacccatc   2160

tccaggacca agcgctctga gccctggatc tagcggactg agcaacagcc acacacctgt   2220

gcggcctcca agcacaagca gcacaggctc tagaggaagc tgtggcagca gcggaagaac   2280

cgccgaaaag accagcctga gcttcaagag cgaccaagtg aaagtgaaac aagagcccgg   2340

caccgaggac gagatctgca gtttttctgg cggcgtgaag caagagaaaa ccgaggatgg   2400

gagaagatct gcctgcatgc tgagcagccc tgagagcagc cttacacctc cactgagcac   2460

caacctgcac ctggaaagcg aactggatgc cctggcctct ctggaaaacc acgtgaaaac   2520

agagcccgcc gacatgaacg agagctgcaa gcagtctgga ctgtccagcc tggtcaacgg   2580

caagtcccct atccgcagcc tgatgcacag aagcgctaga attggcggcg acggcaacaa   2640

caaggacgac gaccctaacg aggattggtg cgccgtctgt cagaacggcg gagatctgct   2700

gtgttgcgag aagtgcccca aggtgttcca cctgacctgc cacgttccaa cactgctgtc   2760

tttccccagc ggcgactgga tctgtacctt ctgtagagac atcggcaagc ccgaggtgga   2820

atacgactgc gacaatctgc agcactccaa aaagggcaaa acagcccagg gactgagccc   2880

cgtggatcag agaaagtgcg agagactgct gctgtacctg tactgccacg agctgagcat   2940

cgagttccaa gagccagtgc ctgccagcat tcccaactac tacaagatca tcaagaaacc   3000

gatggacctg agcaccgtca agaagaagct gcagaagaag cactcccagc actatcagat   3060

ccccgacgac ttcgtggctg acgtgcgcct gatctttaag aactgcgagc ggttcaatga   3120

gatgatgaag gtggtgcagg tctacgccga cacacaagag attaacctga aagccgacag   3180

cgaggtggcc caggccggaa aagctgtcgc cctgtacttc gaggacaagc tgaccgagat   3240

ctacagcgac cggacattcg ctcctctgcc agagtttgag caagaagagg acgacgggga   3300

agtgaccgag gacagcgacg aggatttcat ccagcctcgg cggaagagac tgaagtccga   3360

tgagcggcca gtgcacatca aatga                                         3385
```

```
<210> SEQ ID NO 2
<211> LENGTH: 857
<212> TYPE: DNA
<213> ORGANISM: Artificial Sequence
<220> FEATURE:
<223> OTHER INFORMATION: codon optimization of TIF1gamma N term sequence

<400> SEQUENCE: 2

tgtgctgttt gtcagcagag cctgcagagc agaagagagg ccgagcctaa gctgctgcct     60

tgcctgcaca gcttctgcct gagatgtctg cccgagcctg agagacagct gagcgttcca    120

attcctggcg gcagcaacgg cgacatccag caagtgggag tgatcagatg ccccgtgtgc    180

tgcaccagct gcgaggacaa tgcctctgcc gtgggcttct gtgtggaatg tggcgagtgg    240

ctgtgcaaga cctgtatcga ggcccaccag agagtgaagt tcaccaagga ccacgccccg    300

tgcacaagca agagcagctg aagctgttct gcgagacatg cgaccggctg acctgcagag    360

attgccagct gctggaacac aaagagcatc tggaagaggc ctttcagaac cagaagggcg    420

ccatcgagaa cctgctggcc aaactgctgg aaaagaaaaa ctacgtgcac ttcgccgcca    480

cacaggtgca gaaccggatc aaagaagtga acgagacaaa caagcgggtc gagcaagaga    540

tcaaggtggc catcttcacc ctgatcaacg agatcaacaa gaagggcaag agcctcctgc    600

agcagctcga gaacgtgacc aaagaacggc agatgaagct gctccagcag cagaacgata    660
```

```
tcaccggcct gagccggcaa gtgaagcacg tgatgaattt caccaactgg gccattgcca    720

gcggctctag cacagccctg ctgtactcca agcggctgat caccttccag ctgcggcaca    780

tcctggccat ccggttccac tgcgacccta ccttttgggc caagaacgtg gtcaacctgg    840

gcaacctggt catcgag                                                    857
```

<210> SEQ ID NO 3
<211> LENGTH: 411
<212> TYPE: DNA
<213> ORGANISM: Artificial Sequence
<220> FEATURE:
<223> OTHER INFORMATION: codon optimization of TIF1gamma C term sequence

<400> SEQUENCE: 3

```
tgcgccgtct gccagaacgg cggagatctg ctgtgttgcg agaagtgccc caaggtgttc     60

cacctgacct gccacgttcc aacactgctg agcttcccta gcggcgactg gatctgcacc    120

ttctgccagg gactgagccc cgtggatcag agaaagtgcg agagactgct gctctacctg    180

tactgccacg agctgagcat cgagttccaa gagcctgtgc ctgccagcat tcccaactac    240

tacaagatca tcaagaaacc catggacctg agcaccgtga agaagaagct gcagaagaag    300

cacagccagc actatcagat ccccgacgac ttcgtggctg acgtgcggct gatcttcaag    360

aactgcgagc ggttcaacga gatgatgaag gtggtgcagg tctacgccga c             411
```

<210> SEQ ID NO 4
<211> LENGTH: 2778
<212> TYPE: DNA
<213> ORGANISM: Artificial Sequence
<220> FEATURE:
<223> OTHER INFORMATION: codon optimization of TIF1gamma N and C term
      sequence

<400> SEQUENCE: 4

```
tgtgctgttt gtcagcagag cctgcagagc agaagagagg ccgagcctaa gctgctgcct     60

tgcctgcaca gcttctgcct gagatgtctg cccgagcctg agagacagct gagcgttcca    120

attcctggcg gcagcaacgg cgacattcag caagtgggcg tgatcagatg ccccgtgtgc    180

agacaagagt gccggcagat tgacctggtg gacaactact tcgtgaagga caccagcgag    240

gcccctagca gctctgacga gaagtctgag caagtgtgca cctcctgcga ggacaatgcc    300

tctgccgtgg gcttctgtgt ggaatgtggc gagtggctgt gcaagacctg tatcgaggcc    360

caccagagag tgaagttcac caaggaccac ctgatccgga agaaagaaga tgtgtccgag    420

agcgtgggcg cctctggaca aagacctgtg ttctgccccg tgcacaagca agagcagctg    480

aagctgttct gcgagacatg cgaccggctg acctgcagag attgccagct gctcgaacac    540

aaagagcaca gataccagtt tctggaagag gcctttcaga accagaaggg cgccatcgag    600

aacctgctgg ccaaactgct ggaaaagaaa aactacgtgc acttcgccgc cacacaggtg    660

cagaaccgga tcaaagaagt gaacgagaca aacaagcggg tcgagcaaga gatcaaggtg    720

gccatcttca ccctgatcaa cgagatcaac aagaagggca agagcctcct gcagcagctg    780

gaaaacgtga ccaaagaacg gcagatgaag ctgcttcagc agcagaacga catcaccggc    840

ctgagcagac aagtgaagca cgtgatgaat ttcaccaact gggccattgc cagcggcagc    900

tctacagccc tgctgtactc caagcggctg atcaccttcc agctgagaca catcctgaag    960

gccagatgcg atcctgtgcc tgccgccaat ggcgctatca gattccactg cgaccccacc   1020

ttttgggcca agaacgtcgt gaacctgggc aacctggtca tcgagagcaa gcctgctcct   1080
```

-continued

```
ggctacaccc ctaatgtggt cgttggacag gtgccacctg gcaccaacca catctctaag   1140

acccctggcc agatcaacct ggctcagctc agactgcagc acatgcagca gcaagtgtac   1200

gcccagaaac accagcagct gcagcagatg cggatgcagc aacctcctgc tccagtgcct   1260

accaccacca caaccacaca gcagcaccct agacaggccg ctcctcagat gctgcaacag   1320

cagcctccaa gactgatcag cgtgcagact atgcagcggg gcaacatgaa ctgcggagcc   1380

tttcaggccc atcagatgag actggcccag aacgccgcta gaatccctgg catccctaga   1440

cacagcggcc ctcagtacag catgatgcag ccccatctgc agagacagca cagcaatcct   1500

ggacacgccg gaccttttcc agtggtgtct gtgcacaata ccacgatcaa ccctacaagc   1560

cccaccaccg ccacaatggc caatgccaat agaggcccaa caagccctag cgtgacagcc   1620

atcgagctga tccccagcgt gacaaacccc gagaatctgc ctagcctgcc tgacatccct   1680

cctatccagc tcgaggatgc cggctctagc agcctggata atctgctgag ccggtacatc   1740

agcggctccc atcttccacc tcagcctacc agcacaatga acccatctcc aggaccaagc   1800

gctctgagcc ctggatctag cggactgagc aacagccaca cacctgtgcg gcctccaagc   1860

acaagcagca caggctctag aggaagctgt ggcagcagcg gaagaaccgc cgaaaagacc   1920

agcctgagct tcaagagcga ccaagtgaaa gtgaaacaag agcccggcac cgaggacgag   1980

atctgcagtt tttctggcgg cgtgaagcaa gagaaaaccg aggatgggag aagatctgcc   2040

tgcatgctga gcagccctga gagcagcctt acacctccac tgagcaccaa cctgcacctg   2100

gaaagcgaac tggatgccct ggcctctctg gaaaaccacg tgaaaacaga gcccgccgac   2160

atgaacgaga gctgcaagca gtctggactg tccagcctgg tcaacggcaa gtcccctatc   2220

cgcagcctga tgcacagaag cgctagaatt ggcggcgacg gcaacaacaa ggacgacgac   2280

cctaacgagg attggtgcgc cgtctgtcag aacggcggag atctgctgtg ttgcgagaag   2340

tgccccaagg tgttccacct gacctgccac gttccaacac tgctgtcttt ccccagcggc   2400

gactggatct gtaccttctg tagagacatc ggcaagcccg aggtggaata cgactgcgac   2460

aatctgcagc actccaaaaa gggcaaaaca gcccagggac tgagccccgt ggatcagaga   2520

aagtgcgaga gactgctgct gtacctgtac tgccacgagc tgagcatcga gttccaagag   2580

ccagtgcctg ccagcattcc caactactac aagatcatca agaaaccgat ggacctgagc   2640

accgtcaaga agaagctgca gaagaagcac tcccagcact atcagatccc cgacgacttc   2700

gtggctgacg tgcgcctgat ctttaagaac tgcgagcggt tcaatgagat gatgaaggtg   2760

gtgcaggtct acgccgac                                                 2778
```

<210> SEQ ID NO 5
<211> LENGTH: 470
<212> TYPE: DNA
<213> ORGANISM: Artificial Sequence
<220> FEATURE:
<223> OTHER INFORMATION: human TGF promoter

<400> SEQUENCE: 5

```
gtcgactgac agaccctctt ctcctacctt gtttcccagc ctgactctcc ttccgttctg     60

ggtccccctc ctctggtcgg ctcccctgtg tctcatcccc cggattaagc cttctccgcc    120

tggtcctctt tctctggtga cccacaccgc ccgcaaagcc acagcgcatc tggatcaccc    180

gctttggtgg cgcttggccg ccaggaggca gcaccctgtt tgcggggcgg agccggggtg    240

cccgcccccct ttcccccagg gctgaaggga cccccctcgg agcccgccca cgcgagatga    300

ggacggtggc ccagcccccc catgccctcc ccctgggggc cgcccccgct cccgccccgt    360
```

-continued

```
gcgcttcctg ggtggggccg ggggcggctt caaaaccccc tgccgaccca gccggtcccc    420

gccgccgccg cccttcgcgc cctgggccat ctccctccca cctccctccg              470
```